United States Patent
Yousef et al.

(10) Patent No.: US 10,466,188 B2
(45) Date of Patent: Nov. 5, 2019

(54) THERMAL SIMULATOR

(71) Applicant: OHIO STATE INNOVATION FOUNDATION, Columbus, OH (US)

(72) Inventors: Ahmed Yousef, Dublin, OH (US);
David Kasler, Ashville, OH (US);
Mohammad Shavezipur, Columbus, OH (US)

(73) Assignee: OHIO STATE INNOVATION FOUNDATION, Columbus, OH (US)

(*) Notice: Subject to any disclaimer, the term of this patent is extended or adjusted under 35 U.S.C. 154(b) by 309 days.

(21) Appl. No.: 15/399,777

(22) Filed: Jan. 6, 2017

(65) Prior Publication Data

US 2017/0115244 A1 Apr. 27, 2017

Related U.S. Application Data

(62) Division of application No. 13/920,165, filed on Jun. 18, 2013, now Pat. No. 9,568,457.

(51) Int. Cl.
| | |
|---|---|
| *G01K 3/00* | (2006.01) |
| *G01N 25/00* | (2006.01) |
| *G01N 33/08* | (2006.01) |
| *A23L 15/00* | (2016.01) |
| *G01K 13/12* | (2006.01) |
| *G01K 7/02* | (2006.01) |

(52) U.S. Cl.
CPC .............. *G01N 25/00* (2013.01); *A23L 15/35* (2016.08); *G01K 7/02* (2013.01); *G01K 13/12* (2013.01); *G01N 33/08* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 3,974,296 A | * | 8/1976 | Burkwall, Jr. | ......... A23K 10/20 426/104 |
| 4,077,259 A | * | 3/1978 | Foster | ...................... G01K 1/14 374/134 |
| 5,620,735 A | * | 4/1997 | Manderfeld | ........... A23B 5/041 426/512 |
| 6,406,727 B1 | * | 6/2002 | Hamid-Samimi | ....... A23B 5/01 426/234 |
| 6,692,784 B2 | * | 2/2004 | Davidson | ............. A23B 5/0052 426/298 |

(Continued)

*Primary Examiner* — Lisa M Caputo
*Assistant Examiner* — Nasir U. Ahmed
(74) *Attorney, Agent, or Firm* — Fay Sharpe LLP

(57) ABSTRACT

A thermal simulator simulates the thermal behavior of items such as eggs for which the actual internal temperature profile is difficult to measure. A yolk body simulates the egg yolk, an albumen body surrounds the yolk body and simulates the egg albumen, and a shell layer surrounds the albumen body to simulate the shell. The thermal properties of the materials forming the egg body, albumen body and shell layer are tuned to match the thermal properties of the egg yolk, egg albumen and egg shell. Thermometric devices are positioned within the egg body and egg albumen along with communication devices which process signals from the thermometric devices indicative of temperature and communicate these signals to a computer for further processing and display.

50 Claims, 6 Drawing Sheets

(56) References Cited

U.S. PATENT DOCUMENTS 6,800,315 B2* 10/2004 Yousef ................. A23B 5/0052
426/248
2004/0058040 A1* 3/2004 Park ..................... A23B 5/0052
426/298

* cited by examiner

THERMAL SIMULATOR

CROSS-REFERENCE TO RELATED APPLICATIONS

This application is a divisional application of U.S. patent application Ser. No. 13/920,165, filed Jun. 18, 2013, the contents of which are incorporated by reference herein in its entirety.

FIELD OF THE INVENTION

This invention concerns devices for simulating the thermal characteristics of items for which direct measurement of the item's internal temperature is difficult.

BACKGROUND

Federal mandates passed in 2009 require whole shell egg producers to take numerous precautions to help prevent *Salmonella enterica* serovar *Enteritidis* in egg laying flocks. The Food and Drug Administration (FDA) reports as many as 79,000 illnesses and 30 deaths could be prevented each year if such precautions are implemented. The FDA mandates require periodic *Salmonella* testing, cleaning and sanitizing of positive houses, and impose protocols for preventing the introduction and spread of bacteria, pest control, as well as protocols for workers and equipment. Additional record keeping requirements are also part of the mandates.

However, these mandates are not required if the eggs are subjected to a pasteurization process before they are sold to consumers. While several procedures using different techniques exist, such as microwave, radio wave, ozone, and basic convective heat treatments for pasteurizing whole shell eggs, only one of the methods is used commercially in the United States today. Although these decontamination processes vary significantly, all rely on heating the eggs, either fully or partially, to ensure proper reduction of the *Salmonella* population.

An example pasteurization process reveals some of the complications associated with methods that primarily use heat. The heat of the pasteurization process partially denatures egg proteins and changes the functionality of raw egg components. Lack of effective temperature monitoring and control increases the severity of these changes. Egg processors need to ensure that the thermal treatment is stringent enough to eliminate internal egg pathogens without causing thermal damage to egg components. Therefore, there is a need to accurately measure and promptly report internal egg temperature during the heating process. Current techniques to monitor an egg's internal temperature are cumbersome and often produce inconsistent results. Indirect methods of process control include regulating the temperature of a water bath in which the eggs are heated and regulating the time which the eggs spend in the bath. However, even these measurements are usually derived from those taken previously from the egg itself and are thus less than reliable.

Currently, the thermal processing of eggs is monitored using technologies developed for the canning industry. An example of this conventional temperature monitoring involves using thermocouples inserted inside the coldest spot of a number of test eggs, and locating the test eggs in the least-heated position in the apparatus heating the eggs, such as a water bath. Long wires transmit thermocouple signals from test eggs to signal reading devices and a data processing system located outside of the water bath. The data processing system amplifies the thermocouple signals, an analog-to-digital converter digitizes the signals, and computer software transforms the digitized signals to a temperature-time matrix.

Measuring internal egg temperature involves positioning a thermocouple in egg's coldest spot, which is an imprecise exercise. The egg shell is solid layer that is suitable for protecting potentially developing embryo. The shell keeps fluid parts in and extraneous substances out. Because the shell is made of a brittle porous material, inserting a temperature probe into the egg without cracking it is an art that takes time and many failures to master. Once inserted, the shell is not strong enough to reliably maintain the orientation of the probe or its position inside the egg. Therefore, a device is needed to hold the egg and temperature probe in the desired orientation and relative position. Consistency of probe orientation and position is also crucial. The center of the yolk heats much more slowly than the region at its boundary with the albumen just outside the yolk. Inconsistency of temperature probe position can produce errors that would adversely affect process lethality or product quality.

There is clearly a need for a device which can replace the use of actual eggs to monitor and control the internal temperature of eggs subjected to pasteurization processes.

SUMMARY

One example concept of the invention concerns a thermal simulator for an egg having a yolk, an albumen layer and a shell. In one example embodiment, the thermal simulator comprises a yolk body simulating the yolk. An albumen body simulating the albumen surrounds the yolk body. A shell layer may surround the albumen body. The shell layer simulates the shell. A first thermometric device is positioned within either the yolk body or the albumen body. A first communication device is positioned within one of the yolk body or the albumen body for transmitting a first temperature, measured within either the yolk body or the albumen body, by the first thermometric device, to a position outside of the shell layer.

In a particular example embodiment, the first thermometric device and the first communication device are positioned within the yolk body. In this example, the thermal simulator further comprises a second thermometric device positioned within the albumen body. A second communication device is positioned within the albumen body for transmitting a second temperature, measured within the albumen body by the second thermometric device, to a position outside of the thermal simulator.

In order to simulate the yolk, the yolk body comprises a material having a thermal diffusivity from about 1.1E-07 to about 1.4E-07 m$^2$/s. In a specific example embodiment, the yolk body comprises a material having a thermal diffusivity of about 1.3E-07. In order to simulate the yolk, the yolk body comprises a material having a heat capacity from about 1000 to about 4000 J/(kg*K). In a specific example embodiment, the yolk body comprises a material having a heat capacity of about 2700 J/(kg*K). In order to simulate the albumen, the albumen body comprises a material having a thermal diffusivity from about 1.3E-07 to about 2.3E-07 m$^2$/s. In a specific example embodiment, the albumen body comprises a material having a thermal diffusivity of about 2.2E-07 m$^2$/s. In order to simulate the albumen, the albumen body comprises a material having a heat capacity from about 500 to about 4000 J/(kg*K). In a specific example embodiment, the albumen body comprises a material having a heat capacity of about 2900 J/(kg*K). In order to simulate the shell, the shell layer comprises a material having a thermal diffusivity from about 7.0E-08 to about 7.0E-06 m$^2$/s. In a specific example embodiment, the shell layer comprises a material having a thermal diffusivity of about 7.6E-07 m$^2$/s. In order to simulate the shell, the shell layer comprises a material having a heat capacity from about 500 to about 2000 J/(kg*K). In a specific example embodiment, the shell layer comprises a material having a heat capacity of about 910 J/(kg*K). In order to simulate the yolk, the yolk body comprises a material having a density from about 700 to about 4000 kg/m$^3$. In a specific example embodiment, the yolk body comprises a material having a density of about 1100 kg/m$^3$. In order to simulate the albumen, the albumen body comprises a material having a density from about 700 to about 4000 kg/m$^3$. In a specific example embodiment, the albumen body comprises a material having a density of about 1000 kg/m$^3$. In order to simulate the shell, the shell layer comprises a material having a density from about 1000 to about 3000 kg/m$^3$. In a specific example embodiment, the shell layer comprises a material having a density of about 2100 kg/m$^3$. In order to simulate the yolk, the yolk body comprises a material having a thermal conductivity from about 0.2 to about 0.6 W/(m*K). In a specific example embodiment, the yolk body comprises a material having a thermal conductivity of about 0.4 W/(m*K). In order to simulate the albumen, the albumen body comprises a material having a thermal conductivity from about 0.1 to about 0.9 W/(m*K). In a specific example embodiment, the albumen body comprises a material having a thermal conductivity of about 0.6 W/(m*K). In order to simulate the shell, the shell layer comprises a material having a thermal conductivity from about 0.15 to about 2.0 W/(m*K). In a specific example embodiment, the shell layer comprises a material having a thermal conductivity of about 1.5 W/(m*K).

By way of example, the yolk body may comprise a polyamide, the albumen body may comprise epoxy and the shell layer may comprise polytetrafluoroethylene. The yolk body may comprise metal particles or carbon based particles to increase its thermal conductivity, or it may comprise ceramic particles to decrease its thermal conductivity. Similarly, the albumen body may comprise metal particles or carbon based particles to increase its thermal conductivity or it may comprise ceramic particles to decrease its thermal conductivity.

In an example embodiments, the thermometric devices may comprise capacitive sensors piezo-resistive sensors, vibration based sensors and thermocouples.

In a particular example embodiment, the first communication device comprises transduction and signal processing circuitry for converting a temperature measurement into an electric signal, a radio frequency antenna and radio transmitter circuitry for transmitting the electric signal, and an energy storage unit for powering the circuitry. In another example embodiment, the first communication device comprises electrical conductors extending from the first thermometric device to the position outside of the thermal simulator.

In a particular example embodiment, the second communication device comprise transduction and signal processing circuitry for converting a temperature measurement into an electric signal, a radio frequency antenna and radio transmitter circuitry for transmitting the electric signal, and an energy storage unit for powering the circuitry. In another embodiment, the second communication device comprises electrical conductors extending from the first thermometric device to the position outside of the thermal simulator.

By way of example, a plurality of first thermometric devices may be positioned within the yolk body and/or within the albumen body.

Another example concept of the thermal simulator comprises a first body formed of a first material. The first material has a first heat capacity, a first density, and a first thermal conductivity. A first thermometric device is positioned within the first body. A first communication device for transmitting a first temperature, measured within the first body by the first thermometric device, to a position outside of the first body is positioned within the first body. In a particular example embodiment, the first communication device comprises transduction and signal processing circuitry for converting a temperature measurement into an electric signal, a radio frequency antenna and radio transmitter circuitry for transmitting the electric signal, and an energy storage unit for powering the circuitry. In another example embodiment, the first communication device comprises an electrical conductor extending from the first thermometric device through the first body. By way of example, the first thermometric device may comprise a capacitive sensor. In another example embodiment, the first thermometric device may comprise a thermocouple.

By way of example, the thermal simulator may further comprise a second body surrounding the first body. The second body is formed of a second material. The second material has a second heat capacity, a second density, and a second thermal conductivity. A second thermometric device may be positioned within the second body. A second communication device for transmitting a second temperature, measured within the second body by the second thermometric device, to a position outside of the second body, may also be positioned within the second body.

In a particular example embodiment, the first and second bodies are in contact with one another. By way of example, the second material may be different from the first material. By way of further example, at least one of the second heat capacity, the second density, and the second thermal conductivity is different from the first heat capacity, the first density, and the first thermal conductivity respectively.

In a particular example embodiment, the second communication device comprises transduction and signal processing circuitry for converting a temperature measurement into an electric signal, a radio frequency antenna and radio transmitter circuitry for transmitting the electric signal, and an energy storage unit for powering the circuitry. In another example embodiment, the second communication device comprises an electrical conductor extending from the second thermometric device through the second body.

By way of example, the thermal simulator may further comprise a third body surrounding the second body. The third body is formed of a third material. The third material has a third heat capacity, a third density, and a third thermal conductivity. A third thermometric device may be positioned within the third body. A third communication device for transmitting a third temperature, measured within the third body by the third thermometric device, to a position outside of the third body may also be positioned within the third body.

In a particular example embodiment, the second and third bodies are in contact with one another. By way of example, the third material may be different from the second material. In an example embodiment, at least one of the third heat capacity, the third density, and the third thermal conductivity is different from the second heat capacity, the second density, and the second thermal conductivity respectively.

In a particular example embodiment, the third communication device comprises transduction and signal processing circuitry for converting a temperature measurement into an electric signal, a radio frequency antenna and radio transmitter circuitry for transmitting the electric signal, and an energy storage unit for powering the circuitry. In another example embodiment, the third communication device comprises an electrical conductor extending from the third thermometric device through the third body.

In another example concept, the thermal simulator comprises a first substrate formed of a first material, the first material having a first heat capacity, a first density, and a first thermal conductivity. A first thermometric device is positioned within the first substrate. A first communication device for transmitting a first temperature, measured within the first substrate by the first thermometric device, to a position outside of the first substrate is also positioned within the first substrate.

In a particular example embodiment, the first communication device comprises transduction and signal processing circuitry for converting a temperature measurement into an electric signal, a radio frequency antenna and radio transmitter circuitry for transmitting the electric signal, and an energy storage unit for powering the circuitry. In another example embodiment, the first communication device comprises an electrical conductor extending from the first thermometric device through the first substrate.

By way of example, the first thermometric device may comprise a capacitive sensor. In another example embodiment, the first thermometric device comprises a thermocouple.

By way of example, the thermal simulator may further comprise a second substrate overlying the first substrate. The second substrate is formed of a second material. The second material has a second heat capacity, a second density, and a second thermal conductivity. A second thermometric device may be positioned within the second substrate. A second communication device for transmitting a second temperature, measured within the second substrate by the second thermometric device, to a position outside of the second substrate may also be positioned within the second substrate.

In a particular example embodiment, the first and second substrates are in contact with one another. In another example embodiment, the second material is different from the first material. By way of further example, at least one of the second heat capacity, the second density, and the second thermal conductivity is different from the first heat capacity, the first density, and the first thermal conductivity respectively.

In an example embodiment, the second communication device comprises transduction and signal processing circuitry for converting a temperature measurement into an electric signal, a radio frequency antenna and radio transmitter circuitry for transmitting the electric signal, and an energy storage unit for powering the circuitry. In another example embodiment, the second communication device comprises an electrical conductor extending from the second thermometric device through the second substrate.

By way of example, the thermal simulator may further comprise a third substrate overlying the second substrate. The third substrate is formed of a third material. The third material has a third heat capacity, a third density, and a third thermal conductivity. A third thermometric device may be positioned within the third substrate. A third communication device for transmitting a third temperature, measured within the third substrate by the third thermometric device, to a position outside of the third substrate may also be positioned within the third substrate.

In a particular example embodiment, the second and third substrates are in contact with one another. By way of example, the third material may be different from the second material. In a further example, at least one of the third heat capacity, the third density, and the third thermal conductivity is different from the second heat capacity, the second density, and the second thermal conductivity respectively.

In an example embodiment, the third communication device comprises transduction and signal processing circuitry for converting a temperature measurement into an electric signal, a radio frequency antenna and radio transmitter circuitry for transmitting the electric signal, and an energy storage unit for powering the circuitry. In another example embodiment, the third communication device comprises an electrical conductor extending from the third thermometric device through the third substrate.

The invention further comprises another embodiment of a thermal simulator. By way of example, the thermal simulator comprises a shell layer defining an enclosed volume. The shell layer has an inner surface facing the enclosed volume. A first thermometric device is positioned within the enclosed volume. A first communication device is also positioned within the enclosed volume for transmitting a first temperature, measured within the enclosed volume by the first thermometric device, to a position outside of the shell layer. A support structure is positioned between the inner surface of the shell layer and the first thermometric device for fixing the first thermometric device at a desired position within the enclosed volume.

In one example embodiment, the first thermometric device is positioned at a center of the enclosed volume. An example thermal simulator may further comprise a second thermometric device positioned within the enclosed volume. A second communication device may also be positioned within the enclosed volume for transmitting a second temperature, measured within the enclosed volume by the second thermometric device, to a position outside of the shell layer. The second thermometric device may be attached to the inner surface of the shell layer, for example.

In one example thermal simulator, the enclosed volume contains a gas. The gas may comprise air for example. In another example embodiment, the enclosed volume contains a liquid. In yet another example embodiment, the enclosed volume comprises at least a partial vacuum.

In one example embodiment, the support structure comprises at least one strut extending between the inner surface and the first thermometric device. The at least one strut conducts heat from the shell layer to the first thermometric device at a desired rate. In another example embodiment, the support structure may comprise a plurality of wires extending between the shell layer and the first thermometric device, the wires being adapted to conduct heat from the shell to the first thermometric device at a desire rate.

By way of example, the communication devices may comprise transduction and signal processing circuitry for converting a temperature measurement into an electric signal, a radio frequency antenna and radio transmitter circuitry for transmitting the electric signal, and an energy storage unit for powering the circuitry. In another example embodiment, the communication devices may comprise an electrical conductor extending from the first thermometric device through the shell layer. In a practical example, the thermometric devices may comprise a sensor selected from the group consisting of capacitive sensors, piezo-resistive sensors, vibration based sensors and thermocouples.

DETAILED DESCRIPTION

One object of the invention is to provide a device which simulates the thermal behavior of an egg having a yolk, an albumen layer and a shell. The egg thermal simulator disclosed herein is used to predict the temperature distribution within an egg by measuring the temperature distribution within the egg thermal simulator when both the egg and egg thermal simulator are subjected to the same thermal environment. Use of such a simulator, for example, will allow a heat treatment process intended to sterilize the eggs, to be monitored and controlled for efficacy.

Figure 1:
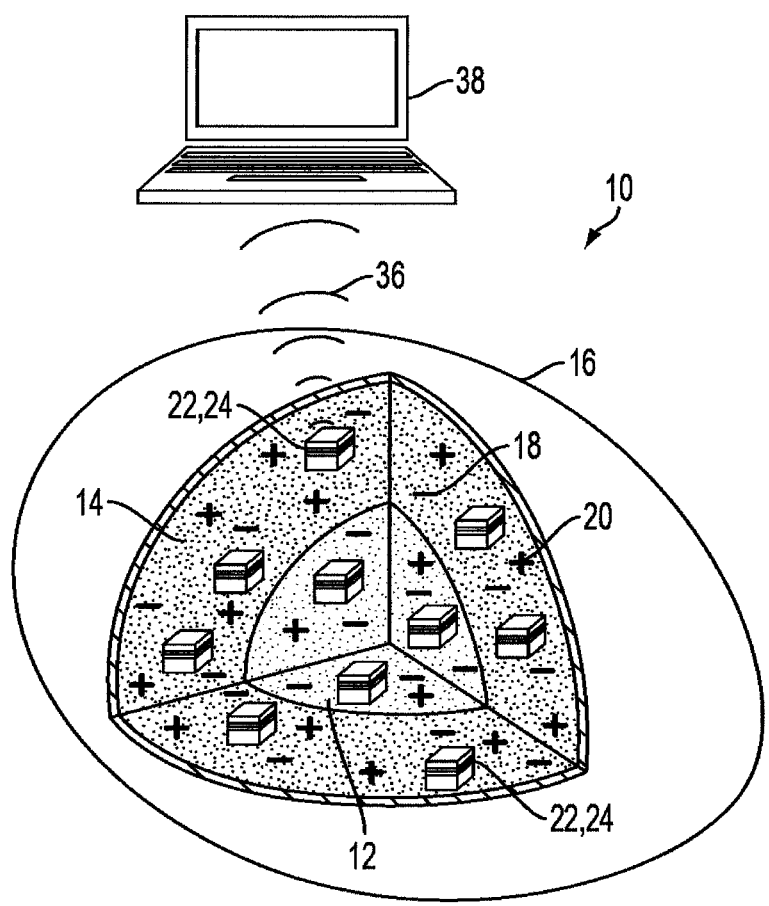
FIG. 1 is an isometric partial sectional view of an example embodiment of a thermal simulator according to the invention.

FIG. 1 shows an example thermal simulator 10 for an egg having a yolk, an albumen layer and a shell. Thermal simulator 10 comprises a yolk body 12 simulating the thermal characteristics of the egg's yolk. Yolk body 12 is surrounded by an albumen body 14 simulating the thermal characteristics of the egg's albumen layer. An optional shell layer 16 may surround the albumen body, the shell layer simulating the thermal characteristics of the egg's shell.

The primary parameter necessary to effectively simulate the thermal characteristics of the egg's yolk, albumen layer and shell is the thermal diffusivity. The heat capacity, the density, and the thermal conductivity of the yolk, albumen layer and shell also play an important part in the simulation. To that end, the yolk body 12 is formed from a material having a thermal diffusivity, heat capacity, density and thermal conductivity matched as closely as possible to that of the egg's yolk. It is expected that a yolk body 12 formed from a material having a thermal diffusivity from about 1.1 E-07 to about 1.4E-07 m$^2$/s, a heat capacity from about 1000 to about 4000 J/(kg*K), a density from about 700 to about 4000 kg/m$^3$, and a thermal conductivity from about 0.2 to about 0.6 W/(m*K) will behave similarly to an egg's yolk so as to provide acceptable predictions of the actual temperature within the egg to which the simulator is matched. Mathematical models predict that polyamide material, specifically Polyamide 610 having a thermal diffusivity of about 1.26E-07 m$^2$/s, a heat capacity of about 1700 J/(kg*K), a density of about 1075 kg/m$^3$, and a thermal conductivity of about 0.23 provide useful results when used to form the yolk body 12.

Similarly, the material for the albumen body 14 is selected so as to match, as closely as possible, the heat capacity, density, and thermal conductivity of the egg's albumen layer. It is expected that a albumen body 14 formed from a material having a thermal diffusivity from about 1.3E-07 to about 2.3E-07 m$^2$/s, a heat capacity from about 500 to about 4000 J/(kg*K), a density from about 700 to about 4000 kg/m$^3$, and a thermal conductivity from about 0.1 to about 0.9 W/(m*K) will behave similarly to an egg's albumen so as to provide acceptable predictions of the actual temperature within the egg to which the simulator is matched. Mathematical models predict that epoxy, specifically diglycidyl ether type epoxy, having a thermal diffusivity of about 2.25E-07 m$^2$/s, a heat capacity of about 636 J/(kg*K), a density of about 1170 kg/m$^3$, and a thermal conductivity of about 0.17 W/(m*K) provides useful results when used to form the albumen body. Silicone gel may also be used as the albumen body 14. The viscous nature of the gel will allow the viscous properties of the albumen layer to be simulated, thus capturing the effects of heat transfer by convection. Note that the shell layer 16 will be used to enclose and contain the albumen body 14 when viscous materials, such as silicone gels are used.

The egg's shell may also have a measurable effect on the heat transfer characteristics of the egg. Therefore, it is advantageous to select a material for the shell layer 16 matching, as closely as possible, the thermal diffusivity, heat capacity, density, and thermal conductivity of the egg's shell. It is expected that a shell layer 16 formed from a material having a thermal diffusivity from about 7E-08 to about 7E-06 m$^2$/s, a heat capacity from about 500 to about 2000 J/(kg*K), a density from about 1000 to about 3000 kg/m$^3$, and a thermal conductivity from about 0.15 to about 2 W/m*K) will behave similarly to an egg's shell so as to provide acceptable predictions of the actual temperature within the egg to which the simulator is matched. It is further predicted that polytetrafluoroethylene (Teflon), having a thermal diffusivity of about 1.1E-07 m$^2$/s, a heat capacity of about 1000 J/(kg*K), a density of about 2280 kg/m$^3$, and a conductivity of about 0.25 W/(m*K) will be an acceptable material for the shell layer as it would provide protection for the lesser chemically resistant thermal components.

It is recognized that it may not be possible to select materials having the characteristics of heat capacity, density and thermal conductivity which will provide an acceptable match to those of the egg's yolk, albumen layer and shell. However, it is possible to modify the material characteristics and achieve a thermal simulator which will provide results that correlate well with measurements taken using eggs. For example, particles 18 may be added to the albumen body 14 and/or the yolk body which increase their thermal conductivity. Candidate materials comprising particles 18 used primarily to increase the thermal conductivity of the body in which they are placed include metals such as stainless steel, steel, nickel, copper, iron, aluminum as well as other metals and metal alloys. Carbon materials such as graphite, graphene, carbon nano-tubes and carbides may also comprise particles 18 which increase the thermal conductivity. Likewise, particles 20 may be added to the albumen body 14 and/or the yolk body 12 to decrease the thermal conductivity of the albumen and yolk bodies. Candidate materials include, for example, ceramics. Particles 18 and 20 may further be used in combination to tune the thermal conductivity of a body. Density and heat capacity will also be affected by the presence of the particles 18 and 20. Mathematical models predict that an albumen body 14 comprised of epoxy with 40% stainless steel particle filler will match the characteristics of an egg's albumen layer and yield acceptable predictions for the temperature distribution throughout an egg. Mathematical models have also been developed which predict that epoxy with 30% nickel particle filler will adequately simulate an egg's albumen layer.

The emphasis on matching the relevant material characteristics of an egg's yolk, albumen layer and shell with those of the thermal simulator's yolk body 12, albumen body 14 and shell layer 16 results from the desire for the thermal simulator to have the same approximate size, shape and weight of the egg which it models. Similarity of size, shape and weight between the thermal simulator 10 and an egg is advantageous because such a simulator will be compatible with existing egg processing equipment such as conveyors, holding racks, water baths, sterilizers and the like. Use of a simulator which closely matches the physical size, shape and weight of an egg would therefore avoid the need to modify the egg processing equipment, which would treat the thermal simulator 10 exactly like the rest of the eggs being processed. However, it is recognized that tuning of the thermal simulator's relevant characteristics of heat capacity, density and thermal conductivity may also be achieved by varying the size and shape of the yolk body 12 as well as the thickness and shape of the albumen body 14 and the shell layer 16. Thus thermal simulators 10 according to the invention may also depart significantly from the particular shape and size of an egg if it is not important that the simulator be compatible with egg processing equipment. In such cases, the thermal characteristics are paramount, and the constraints on matching the physical size, shape and weight of an egg are lifted to achieve a simulator which provides data which correlates well with eggs even if the simulator does not look like an egg.

Having a thermal simulator 10 with relevant characteristics of heat capacity, density and thermal conductivity which yield a temperature profile within the yolk body 12 and albumen body 14 that closely approximates the temperature profile within an egg subject to the same thermal environment, it is necessary to measure the temperature profile and communicate the measurements so that an evaluation of the efficacy of the heat treatment process can be made, and or the process may be monitored and controlled. As shown in FIG. 1, one or more thermometric devices 22 may be positioned within the yolk body 12 and/or the albumen body 14 to measure the temperature at one or more points within the simulator 10. In its simplest form, one thermometric device 22 may be positioned within the yolk body 12 to measure the temperature therein and predict the temperature within eggs subject to the same heat treatment process. It may, however, be advantageous to position multiple thermometric devices 22 within the yolk body 12 and/or the albumen body 14 as shown so that a more comprehensive temperature profile may be obtained. Thermometric devices 22 may comprise, for example, miniaturized temperature sensors including capacitive sensors, piezo-resistive sensors, vibration based sensors as well as thermocouples for measuring temperature. It is advantageous that the thermometric devices be as small as possible so as not to adversely affect the thermal or physical characteristics of the simulator 10.

Figure 2:
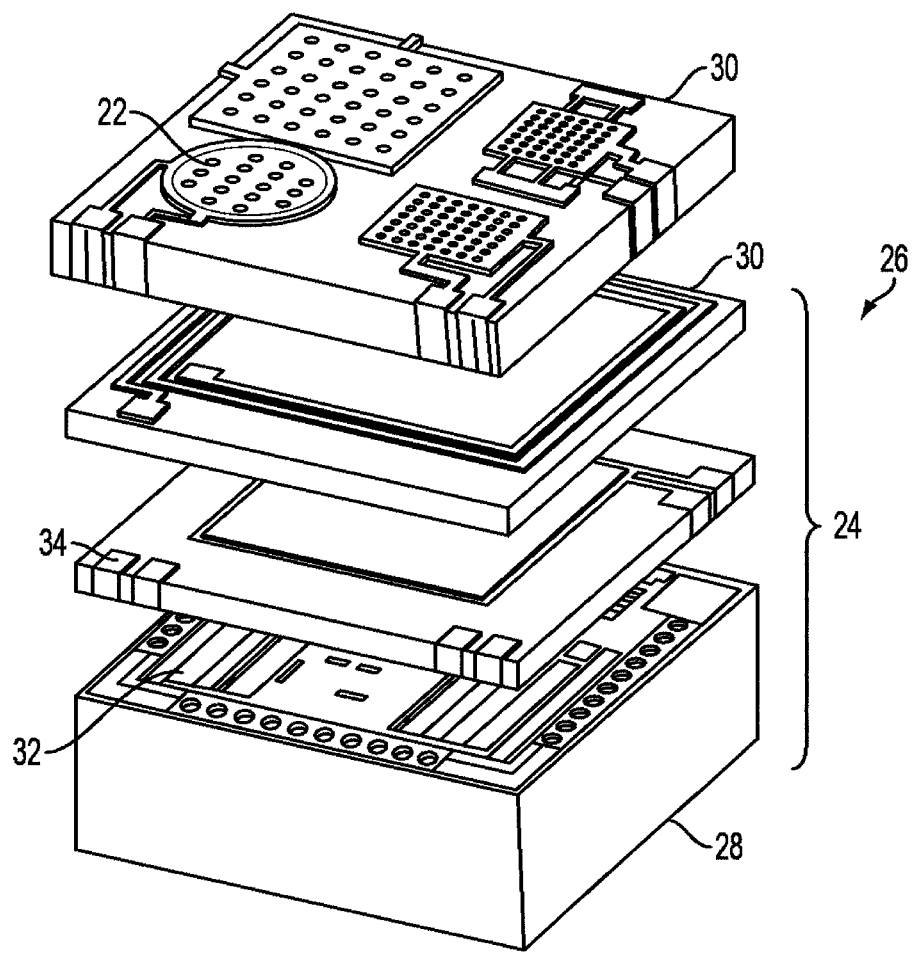
FIG. 2 is an exploded schematic isometric view of a combination thermometric device and communication device used with the thermal simulator of FIG. 1.

Thermometric devices 22 are advantageously operatively associated with communication devices 24 in a combination device 26. An example of a combination device 26 comprising a thermometric device 22 and communication device 24 is shown in FIG. 2. The combination device comprises four main components: the temperature sensor (thermometric device 22), transduction and signal processing circuitry 28, radio frequency antenna 30 and its associated transmission circuitry 32, and an energy storage unit 34. To make the combination device 26 as small as possible microelectromechanical systems (MEMS) technology may be used. For example, the transduction circuitry 28, which performs the function of transducing, filtering and amplifying signals from the temperature sensor 22 may be formed on a CMOS chip. Similarly, the radio transmission circuitry 32 may also be included in the CMOS chip. The CMOS based circuitry 28 and 32 are integrated with the antenna 30 and the temperature sensor 22, and all are powered by the energy storage unit 34. In this example the energy storage unit 34 comprises an electrical battery or super capacitors which may be recharged from outside of the thermal simulator 10 inductively through the antenna. In operation, as shown in FIGS. 1 and 2, signals from the temperature sensor 22 indicative of the temperature within the simulator 10 are processed by the transduction circuitry 28 and fed to the radio transmission circuitry, which transmits the processed signals wirelessly via radio waves 36 to a computer 38 where the processed signals may be stored, displayed, and further manipulated to evaluate the process to which the eggs are subjected.

Figure 3:
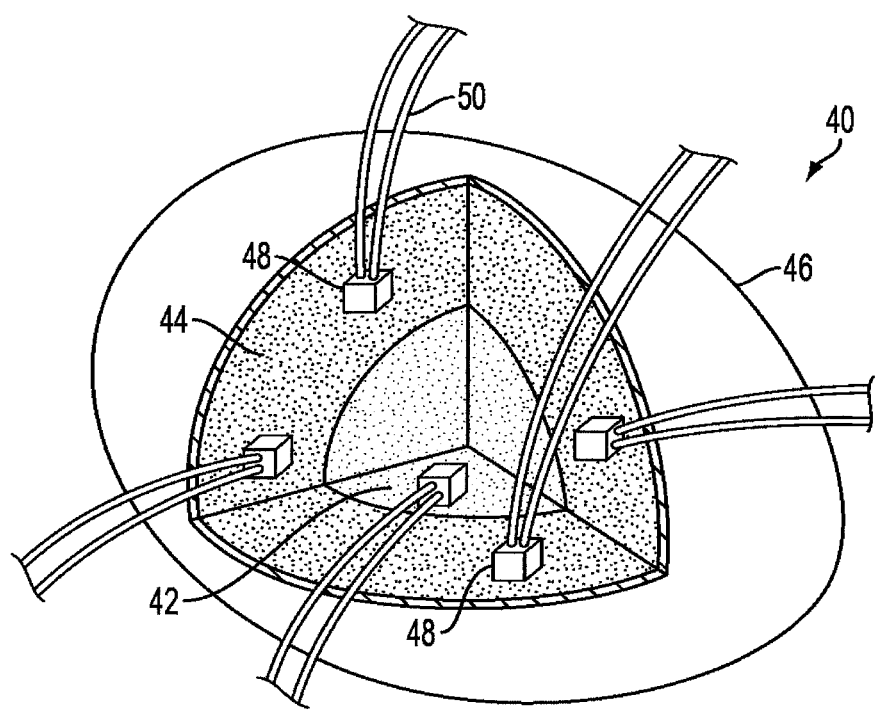
FIG. 3 is an isometric partial sectional view of another example embodiment of a thermal simulator according to the invention.

FIG. 3 illustrates another example embodiment of a thermal simulator 40 according to the invention. Simulator 40 comprises a yolk body 42, albumen body 44 and (optionally) a shell layer 46 substantially as described above, but has a thermometric device 48 coupled to a communication device 50 comprising electrical conductors extending to a position outside of the thermal simulator 40. In this example the thermometric device 48, for example, a thermocouple, generates electrical signals indicative of the temperature within the simulator 40, and the signals are communicated over the electrical conductors 50 (for example, wires) to external processing circuitry (not shown) from whence the processed signals may be further transmitted to a computer for storage, display and further processing.

Figure 4:
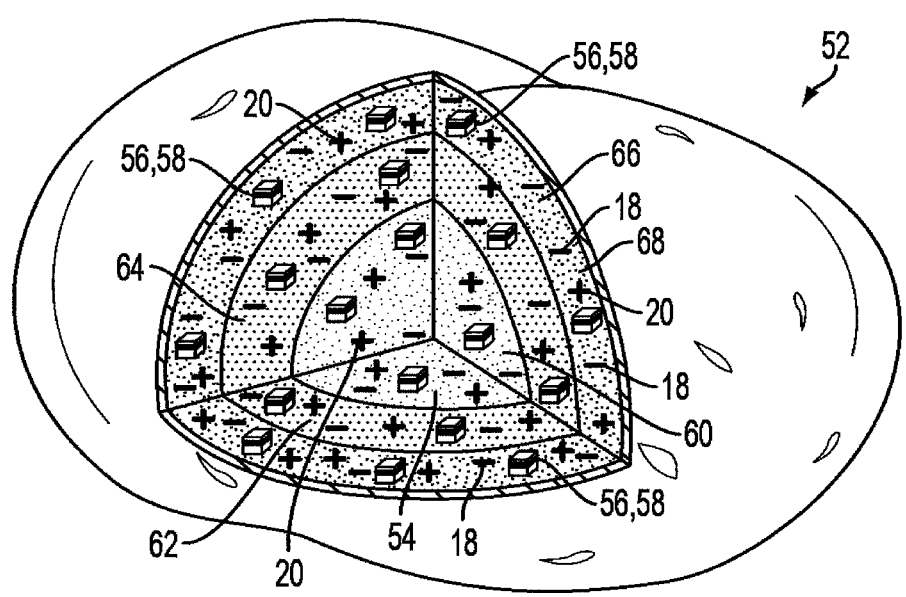
FIG. 4 is an isometric partial sectional view of another example embodiment of a thermal simulator according to the invention.

Although thermal simulators 10 and 40 for an egg have thus far been described, the thermal simulator concept disclosed herein is not limited to these examples, but may be extended to simulate other items almost without limit. FIG. 4 illustrates a generic thermal simulator 52 which may comprise a first body 54 having a thermometric device 56 and a communication device 58 embedded therein. The thermometric device 56 and communication device 58 may be similar to those described above. First body 54 is formed of a first material 60 having a first heat capacity, a first density and a first thermal conductivity, the material 60 being chosen and/or modified (for example by the addition of metal particles 18 and/or ceramic particles 20) so that it simulates the characteristics of a target item. for example, for certain applications it may be feasible to simulate a shell egg by a simulator having a single body 54 which accurately represents the entire egg structure.

A multi-layer item may be simulated by surrounding first body 54 by a second body 62. Second body 62 is formed of a second material 64 having a second heat capacity, a second density and a second thermal conductivity, the second material 62 being chosen and/or modified (for example by the addition of metal particles 18 and/or ceramic particles 20) so that it simulates the characteristics of a particular layer of the target item. The second material 62 may be different from the first material 60 and any one, several, or all of its characteristics of heat capacity, density and thermal conductivity may be different from those of the first material 60. Although the first and second bodies 54 and 62 are shown in contact with one another, they need not be. The second body 62 may also contain thermometric devices 56 and communication devices 58 similar to those described above.

It is clearly feasible to simulate a multi-layer item by the addition of further surrounding bodies. FIG. 4 shows the simulator embodiment 52 having a third body 66 surrounding the second body 62. Third body 66 is formed of a third material 68 having a third heat capacity, a third density and a third thermal conductivity, the third material 68 being chosen and/or modified (for example by the addition of metal particles 18 and/or ceramic particles 20) so that it simulates the characteristics of a particular layer of the target item. The third material 68 may be different from the first material 60 and the second material 64 and any one, several, or all of its characteristics of heat capacity, density and thermal conductivity may be different from those of the first material 60 and/or the second material 62. Although the second and third bodies 62 and 66 are shown in contact with one another, they need not be. The third body may also contain thermometric devices 56 and communication devices 58 similar to those described above. Additional bodies may be added as needed to practical limits.

Figure 5:
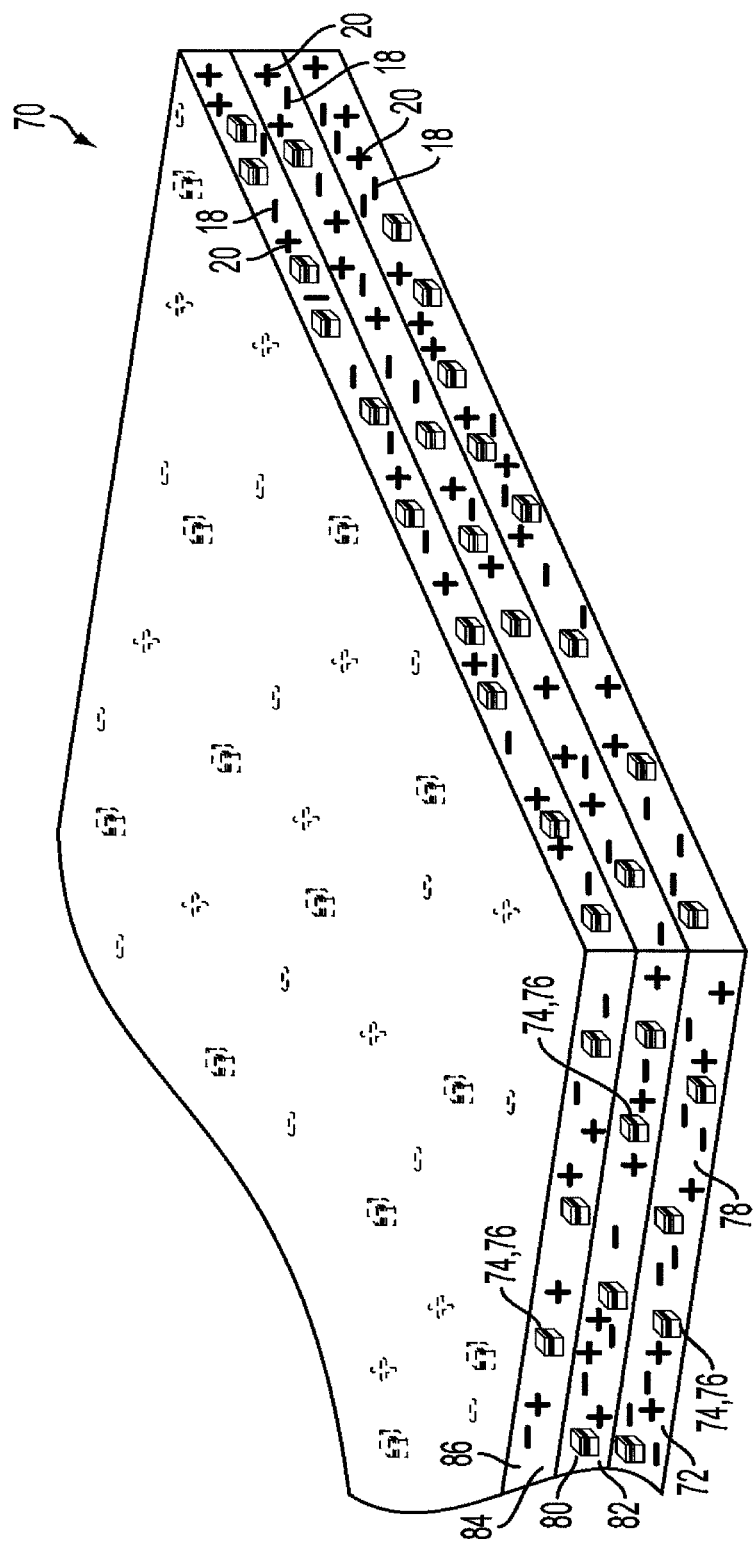
FIG. 5 is an isometric schematic view of another example embodiment of a thermal simulator according to the invention.

While the thermal simulators thus far described are appropriate for modeling three dimensional bodies, the concept is further extendible to "two dimensional" items, i.e., items having a length and width which are significantly greater than their thickness. FIG. 5 illustrates an example thermal simulator embodiment 70 suitable for modeling two dimensional items. Thermal simulator 70 may comprise a first substrate 72 having one or more thermometric devices 74 and communication devices 76 embedded therein. The thermometric device 74 and communication device 76 may be similar to those described above. First substrate 72 is formed of a first material 78 having a first heat capacity, a first density and a first thermal conductivity, the first material 78 being chosen and/or modified (for example by the addition of metal particles 18 and/or ceramic particles 20) so that it simulates the characteristics of a target two dimensional item. A multi-layer item may be simulated by positioning a second substrate 80 overlying the first substrate 72. Second substrate 80 is formed of a second material 82 having a second heat capacity, a second density and a second thermal conductivity, the second material 82 being chosen and/or modified (for example by the addition of metal particles 18 and/or ceramic particles 20) so that it simulates the characteristics of a particular layer of the target item. The second material 82 may be different from the first material 78 and any one, several, or all of its characteristics of heat capacity, density and thermal conductivity may be different from those of the first material 78. Although the first and second substrates 72 and 80 are shown in contact with one another, they need not be. The second substrate may also contain thermometric devices 74 and communication devices 76 similar to those described above.

It is clearly feasible to simulate a multi-layer item by the addition of further substrates. FIG. 5 shows the thermal simulator embodiment 70 having a third substrate 84 positioned overlying the second substrate 80. Third substrate 84 is formed of a third material 86 having a third heat capacity, a third density and a third thermal conductivity, the material 86 being chosen and/or modified (for example by the addition of metal particles 18 and/or ceramic particles 20) so that it simulates the characteristics of a particular layer of the target item. The third material 86 may be different from the first material 78 and the second material 82 and any one, several, or all of its characteristics of heat capacity, density and thermal conductivity may be different from those of the first material 78 and/or the second material 82. Although the second and third substrates 80 and 84 are shown in contact with one another, they need not be. The third substrate 84 may also contain thermometric devices 74 and communication devices 76 similar to those described above. Additional substrates may be added as needed to practical limits.

Figure 6:
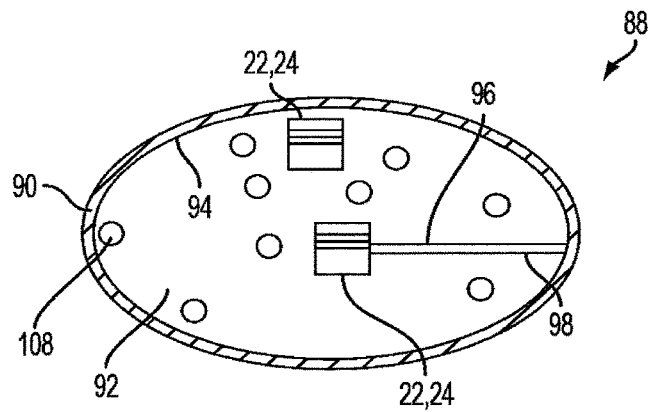
FIGS. 6-8 are cross sectional views of example embodiments of other example embodiments of thermal simulators according to the invention.
Figure 7:
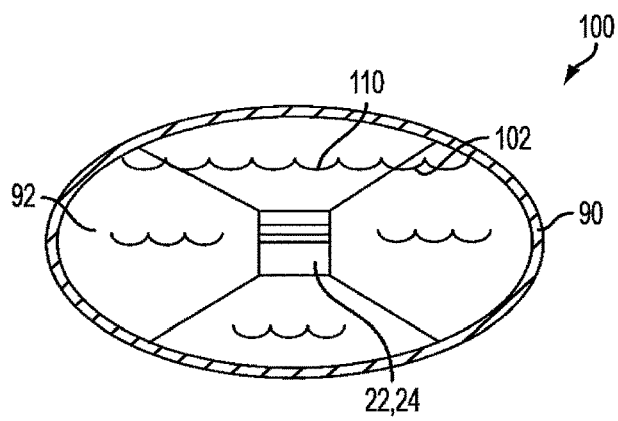
Figure 8:
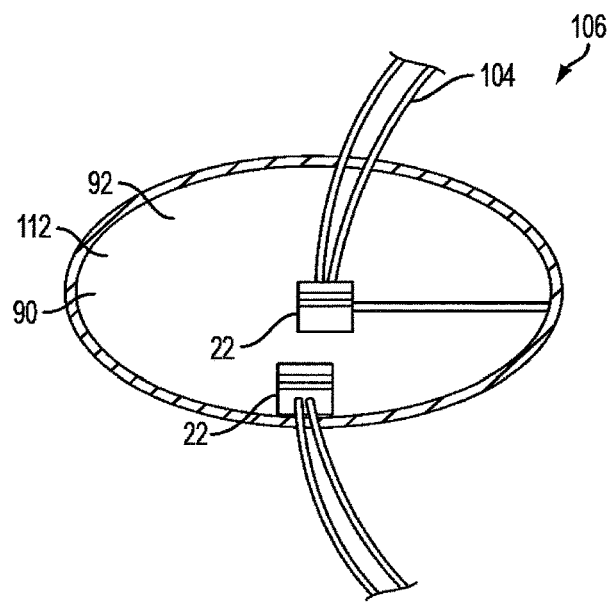

FIGS. 6-8 illustrate additional example thermal simulator embodiments. Thermal simulator 88, shown in FIG. 6, comprises a shell layer 90 which defines an enclosed volume 92. Shell layer 90 has an inner surface 94 that faces the enclosed volume 92. A first thermometric device 22, and a first communication device 24 are positioned within the enclosed volume 92. The thermometric device measures a temperature and the communication device transmits this measurement via radio waves to a position outside of the shell layer 90 as described in detail above. In this example, a support structure 96 is positioned between inner surface 94 and the thermometric device 22 for fixing its position within the enclosed volume 92. In this example, the support structure comprises a strut 98 that is rigidly attached to the shell layer 90 and the thermometric device 22. Strut 98 positions the thermometric device 22 at the center of the enclosed volume 92 in this example, but it could be used to position the device anywhere within the enclosed volume. The strut 98 may be designed so that it conducts heat to the thermometric device at a desired rate so as to simulate the heat transfer characteristics of a particular item. The design parameters which will allow the heat transfer characteristics of the strut to be adjusted include the length, the cross sectional area and the type of material. Through judicious choice of these parameters a wide range of heat transfer characteristics may be simulated. As also shown in FIG. 6, thermometric device 22 and communication device 24 may also be attached directly to the inner surface 94 of the shell layer 90.

FIG. 7 shows another example embodiment of a thermal simulator 100 which uses a plurality of wires 102 as the support structure. Wires 102 extend from the shell layer 90 to the thermometric device 22 (and also the communication device 24) to suspend it at a desired position within the enclosed volume 92. Wires 102 may also be designed to transfer heat from the shell layer 90 to the thermometric device 22 at a desired rate, again by adjusting their characteristics such as length, cross sectional area and type of material.

Although wireless communication between the enclosed volume 92 and the ambient is advantageous, it is also possible to use electrical conductors 104, as shown in example simulator 106 in FIG. 8, to transmit temperature measurements from the thermometric device 22. In this example embodiment, conductors 104 are designed so as to have no significant effect on the heat transfer from the ambient to the thermometric device, thereby maintaining the fidelity of the simulator to its intended simulation.

The enclosed volume 92 in the various embodiments 88, 100 and 106 affords another mechanism for control of the simulator's heat transfer characteristics in that the volume may contain a gas 108 (for example, air) as shown in FIG. 6, a liquid 110, as shown in FIG. 7, or at least a partial vacuum 112 as shown in FIG. 8. The "filling" within the enclosed volume 92 may be selected from many different gases, liquids and pressures so as to adjust the heat transfer properties of the simulator as desired. It is advantageous to form the shell layer 90 and, in certain circumstances, the support structure 96 from inert materials, for example, polymers such as polypropylene, polystyrene and polytetrafluoroethylene (Teflon).

Thermal simulators as described herein will permit temperature measurements to be made which accurately and reliably reflect the actual temperatures within items subjected to the same thermal environment as the thermal simulator. Thermal simulators according to the invention are advantageous when used to simulate items, such as eggs, which are difficult to instrument and wherein it is difficult to make direct measurements reliably and accurately.

What is claimed is:

1. A thermal simulator, comprising:
   a first body formed of a first material, said first material having a first heat capacity, a first density, and a first thermal conductivity;
   a first thermometric device positioned within said first body; and
   a first communication device for transmitting a first temperature, measured within said first body by said first thermometric device, to a position outside of said first body.

2. The thermal simulator according to claim 1, wherein said first communication device comprises:
   transduction and signal processing circuitry for converting a temperature measurement into an electric signal;
   a radio frequency antenna and radio transmitter circuitry for transmitting said electric signal; and
   an energy storage unit for powering said circuitry.

3. The thermal simulator according to claim 1, wherein said first communication device comprises an electrical conductor extending from said first thermometric device through said first body.

4. The thermal simulator according to claim 1, wherein said first thermometric devices comprises a sensor selected from the group consisting of capacitive sensors, piezoresistive sensors, vibration based sensors and thermocouples.

5. The thermal simulator according to claim 1, further comprising:
   a second body surrounding said first body, said second body formed of a second material, said second material having a second heat capacity, a second density, and a second thermal conductivity.

6. The thermal simulator according to claim 5, further comprising
   a second thermometric device positioned within said second body; and
   a second communication device positioned within said second body for transmitting a second temperature, measured within said second body by said second thermometric device, to a position outside of said second body.

7. The thermal simulator according to claim 6, wherein said second communication device comprises:
   transduction and signal processing circuitry for converting a temperature measurement into an electric signal;
   a radio frequency antenna and radio transmitter circuitry for transmitting said electric signal; and
   an energy storage unit for powering said circuitry.

8. The thermal simulator according to claim 6, wherein said second communication device comprises an electrical conductor extending from said second thermometric device through said second body.

9. The thermal simulator according to claim 5, wherein said first and second bodies are in contact with one another.

10. The thermal simulator according to claim 5, wherein said second material is different from said first material.

11. The thermal simulator according to claim 5, wherein at least one of said second heat capacity, said second density, and said second thermal conductivity is different from said first heat capacity, said first density, and said first thermal conductivity respectively.

12. The thermal simulator according to claim 5, further comprising:
   a third body surrounding said second body, said third body formed of a third material, said third material having a third heat capacity, a third density, and a third thermal conductivity.

13. The thermal simulator according to claim 12, further comprising:
   a third thermometric device positioned within said third body; and
   a third communication device positioned within said third body for transmitting a third temperature, measured within said third body by said third thermometric device, to a position outside of said third body.

14. The thermal simulator according to claim 13, wherein said third communication device comprises:
   transduction and signal processing circuitry for converting a temperature measurement into an electric signal;
   a radio frequency antenna and radio transmitter circuitry for transmitting said electric signal; and
   an energy storage unit for powering said circuitry.

15. The thermal simulator according to claim 13, wherein said third communication device comprises an electrical conductor extending from said third thermometric device through said third body.

16. The thermal simulator according to claim 12, wherein said second and third bodies are in contact with one another.

17. The thermal simulator according to claim 12, wherein said third material is different from said second material.

18. The thermal simulator according to claim 12, wherein at least one of said third heat capacity, said third density, and said third thermal conductivity is different from said second heat capacity, said second density, and said second thermal conductivity respectively.

19. A thermal simulator, comprising:
   a first substrate formed of a first material, said first material having a first heat capacity, a first density, and a first thermal conductivity;
   a first thermometric device positioned within said first substrate; and
   a first communication device positioned within said first substrate for transmitting a first temperature, measured within said first substrate by said first thermometric device, to a position outside of said first substrate.

20. The thermal simulator according to claim 19, wherein said first communication device comprises:
   transduction and signal processing circuitry for converting a temperature measurement into an electric signal;
   a radio frequency antenna and radio transmitter circuitry for transmitting said electric signal; and
   an energy storage unit for powering said circuitry.

21. The thermal simulator according to claim 19, wherein said first communication device comprises an electrical conductor extending from said first thermometric device through said first substrate.

22. The thermal simulator according to claim 19, wherein said first thermometric device comprises a capacitive sensor.

23. The thermal simulator according to claim 19, wherein said first thermometric device comprises a thermocouple.

24. The thermal simulator according to claim 19, further comprising:
   a second substrate overlying said first substrate, said second substrate formed of a second material, said second material having a second heat capacity, a second density, and a second thermal conductivity.

25. The thermal simulator according to claim 24, further comprising:
a second thermometric device positioned within said second substrate; and
a second communication device positioned within said second substrate for transmitting a second temperature, measured within said second substrate by said second thermometric device, to a position outside of said second substrate.

26. The thermal simulator according to claim 25, wherein said second communication device comprises:
transduction and signal processing circuitry for converting a temperature measurement into an electric signal;
a radio frequency antenna and radio transmitter circuitry for transmitting said electric signal; and
an energy storage unit for powering said circuitry.

27. The thermal simulator according to claim 25, wherein said second communication device comprises an electrical conductor extending from said second thermometric device through said second substrate.

28. The thermal simulator according to claim 24, wherein said first and second substrates are in contact with one another.

29. The thermal simulator according to claim 24, wherein said second material is different from said first material.

30. The thermal simulator according to claim 24, wherein at least one of said second heat capacity, said second density, and said second thermal conductivity is different from said first heat capacity, said first density, and said first thermal conductivity respectively.

31. The thermal simulator according to claim 24, further comprising:
a third substrate overlying said second substrate, said third substrate formed of a third material, said third material having a third heat capacity, a third density, and a third thermal conductivity.

32. The thermal simulator according to claim 31, further comprising:
a third thermometric device positioned within said third substrate; and
a third communication device for transmitting a third temperature, measured within said third substrate by said third thermometric device, to a position outside of said third substrate.

33. The thermal simulator according to claim 32, wherein said third communication device comprises:
transduction and signal processing circuitry for converting a temperature measurement into an electric signal;
a radio frequency antenna and radio transmitter circuitry for transmitting said electric signal; and
an energy storage unit for powering said circuitry.

34. The thermal simulator according to claim 32, wherein said third communication device comprises an electrical conductor extending from said third thermometric device through said third substrate.

35. The thermal simulator according to claim 31, wherein said second and third substrates are in contact with one another.

36. The thermal simulator according to claim 31, wherein said third material is different from said second material.

37. The thermal simulator according to claim 31, wherein at least one of said third heat capacity, said third density, and said third thermal conductivity is different from said second heat capacity, said second density, and said second thermal conductivity respectively.

38. A thermal simulator, comprising:
a shell layer defining an enclosed volume, said shell layer having an inner surface facing said enclosed volume;
a first thermometric device positioned within said enclosed volume;
a first communication device positioned within said enclosed volume for transmitting a first temperature, measured within said enclosed volume by said first thermometric device, to a position outside of said shell layer; and
a support structure positioned between said inner surface of said shell layer and said first thermometric device for fixing said first thermometric device at a desired position within said enclosed volume.

39. The thermal simulator according to claim 38, wherein said first thermometric device is positioned at a center of said enclosed volume.

40. The thermal simulator according to claim 38, further comprising:
a second thermometric device positioned within said enclosed volume;
a second communication device positioned within said enclosed volume for transmitting a second temperature, measured within said enclosed volume by said second thermometric device, to a position outside of said shell layer; and wherein
said second thermometric device is attached to said inner surface of said shell layer.

41. The thermal simulator according to claim 40, wherein at least one of said first and second communication devices comprises:
transduction and signal processing circuitry for converting a temperature measurement into an electric signal;
a radio frequency antenna and radio transmitter circuitry for transmitting said electric signal; and
an energy storage unit for powering said circuitry.

42. The thermal simulator according to claim 40, wherein at least one of said first and second communication devices comprises an electrical conductor extending from said first thermometric device through said shell layer.

43. The thermal simulator according to claim 40, wherein at least one of said first and second thermometric devices comprises a sensor selected from the group consisting of capacitive sensors, piezo-resistive sensors, vibration based sensors and thermocouples.

44. The thermal simulator according to claim 38, wherein said enclosed volume contains a gas.

45. The thermal simulator according to claim 44, wherein said gas comprises air.

46. The thermal simulator according to claim 38, wherein said enclosed volume contains a liquid.

47. The thermal simulator according to claim 38, wherein said enclosed volume comprises at least a partial vacuum.

48. The thermal simulator according to claim 38, wherein said support structure comprises at least one strut extending between said inner surface and said first thermometric device.

49. The thermal simulator according to claim 48, wherein said at least one strut conducts heat from said shell layer to said first thermometric device at a desired rate.

50. The thermal simulator according to claim 38, wherein said support structure comprises a plurality of wires extending between said shell layer and said first thermometric device, said wires being adapted to conduct heat from said shell to said first thermometric device at a desire rate.

* * * * *